US009889015B2

(12) United States Patent
Richter et al.

(10) Patent No.: US 9,889,015 B2
(45) Date of Patent: Feb. 13, 2018

(54) EXPANDABLE COIL SPINAL IMPLANT

(71) Applicant: DePuy Synthes Products, Inc., Raynham, MA (US)

(72) Inventors: Joern Richter, Oberdorf (CH); Jacques Teisen, Oberdorf (CH)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 15/150,504

(22) Filed: May 10, 2016

(65) Prior Publication Data

US 2016/0250032 A1 Sep. 1, 2016

Related U.S. Application Data

(63) Continuation of application No. 13/804,336, filed on Mar. 14, 2013, now Pat. No. 9,358,120.

(51) Int. Cl.
*A61F 2/44* (2006.01)
*A61F 2/46* (2006.01)
(Continued)

(52) U.S. Cl.
CPC .......... *A61F 2/442* (2013.01); *A61B 17/7097* (2013.01); *A61B 17/8811* (2013.01);
(Continued)

(58) Field of Classification Search
CPC ...... A61B 17/7097; A61F 2/44; A61F 2/4405; A61F 2/442; A61F 2/4425; A61F 2/4455;
(Continued)

(56) References Cited

U.S. PATENT DOCUMENTS 3,211,152 A 10/1965 Stern
4,077,394 A * 3/1978 McCurdy ............ A61B 5/0215 600/18
(Continued)

FOREIGN PATENT DOCUMENTS

DE 10 2005 034 529 A1 1/2007
EP 1 913 903 A2 4/2008
(Continued)

OTHER PUBLICATIONS

International Search Report for PCT/US14/021248 dated Jun. 27, 2014 (7 pages).

(Continued)

*Primary Examiner* — Zade Coley
(74) *Attorney, Agent, or Firm* — Nutter McClennen & Fish LLP

(57) ABSTRACT

Coiled spinal implants for disc, vertebral body, and spinal motion segment replacement or reconstruction comprise a plurality of loops and spaces between the loops, with the loops formed of a hollow material and having a plurality of apertures or a longitudinal gap that extend(s) through the sidewalls of the loops and into the hollow center. The coiled implants include one or more balloons within the hollow center, the spaces between the coil loops, and/or within the central void that the coil surrounds. Filling the balloon expands the loops and thereby increases the height of the coil. Bone graft material or bone cement may be deployed from the apertures or gap.

17 Claims, 9 Drawing Sheets

(51) Int. Cl.

| | |
|---|---|
| ***A61B 17/70*** | (2006.01) |
| ***A61B 17/88*** | (2006.01) |
| *A61B 17/02* | (2006.01) |
| *A61F 2/28* | (2006.01) |
| *A61F 2/30* | (2006.01) |

(52) U.S. Cl.

CPC ............ *A61B 17/8855* (2013.01); *A61F 2/44* (2013.01); *A61F 2/441* (2013.01); *A61F 2/4455* (2013.01); *A61F 2/4601* (2013.01); *A61F 2/4611* (2013.01); *A61B 2017/0256* (2013.01); *A61F 2002/2817* (2013.01); *A61F 2002/2835* (2013.01); *A61F 2002/3008* (2013.01); *A61F 2002/30019* (2013.01); *A61F 2002/3052* (2013.01); *A61F 2002/30056* (2013.01); *A61F 2002/30062* (2013.01); *A61F 2002/30092* (2013.01); *A61F 2002/30153* (2013.01); *A61F 2002/30235* (2013.01); *A61F 2002/30263* (2013.01); *A61F 2002/30289* (2013.01); *A61F 2002/30291* (2013.01); *A61F 2002/30331* (2013.01); *A61F 2002/30462* (2013.01); *A61F 2002/30484* (2013.01); *A61F 2002/30556* (2013.01); *A61F 2002/30563* (2013.01); *A61F 2002/30581* (2013.01); *A61F 2002/30583* (2013.01); *A61F 2002/30584* (2013.01); *A61F 2002/30586* (2013.01); *A61F 2002/30588* (2013.01); *A61F 2002/30594* (2013.01); *A61F 2002/30601* (2013.01); *A61F 2002/30677* (2013.01); *A61F 2002/30772* (2013.01); *A61F 2002/30784* (2013.01); *A61F 2002/448* (2013.01); *A61F 2002/4475* (2013.01); *A61F 2002/4627* (2013.01); *A61F 2002/4635* (2013.01); *A61F 2002/4683* (2013.01); *A61F 2002/4688* (2013.01); *A61F 2310/00017* (2013.01); *A61F 2310/00023* (2013.01); *A61F 2310/00047* (2013.01); *A61F 2310/00071* (2013.01)

(58) Field of Classification Search

CPC ........ A61F 2/446; A61F 2/4465; A61F 2/447; A61F 2002/4415; A61F 2002/443; A61F 2002/4435; A61F 2002/444; A61F 2002/4445; A61F 2002/445; A61F 2002/4475; A61F 2002/448; A61F 2002/4485; A61F 2002/449; A61F 2002/4495

USPC ........................................... 623/17.11–17.16

See application file for complete search history.

(56) References Cited

U.S. PATENT DOCUMENTS

| | | | | |
|---|---|---|---|---|
| 4,512,766 | A | 4/1985 | Vailancourt | |
| 4,856,510 | A | 8/1989 | Kowalewski | |
| 5,181,921 | A | 1/1993 | Makita et al. | |
| 5,306,310 | A * | 4/1994 | Siebels | A61F 2/44 623/17.13 |
| 5,423,850 | A | 6/1995 | Berger | |
| 5,772,661 | A | 6/1998 | Michelson | |
| 5,827,289 | A | 10/1998 | Reiley et al. | |
| 6,066,154 | A * | 5/2000 | Reiley | A61B 17/7097 606/192 |
| 6,228,022 | B1 | 5/2001 | Friesem et al. | |
| 6,468,200 | B1 | 10/2002 | Fischi | |
| 6,582,451 | B1 | 6/2003 | Marucci et al. | |
| 6,607,544 | B1 | 8/2003 | Boucher et al. | |
| 6,632,235 | B2 | 10/2003 | Weikel et al. | |
| 6,679,886 | B2 | 1/2004 | Weikel et al. | |
| 6,712,853 | B2 | 3/2004 | Kuslich | |
| 6,811,558 | B2 | 11/2004 | Davison et al. | |
| 7,056,345 | B2 | 6/2006 | Kuslich | |
| 7,074,226 | B2 | 7/2006 | Roehm, III et al. | |
| 7,108,705 | B2 | 9/2006 | Davison et al. | |
| 7,267,687 | B2 * | 9/2007 | McGuckin, Jr. | A61B 17/70 623/17.11 |
| 7,300,456 | B2 | 11/2007 | Andreas et al. | |
| 7,503,920 | B2 | 3/2009 | Siegal | |
| 7,618,367 | B2 | 11/2009 | Martin et al. | |
| 7,618,431 | B2 | 11/2009 | Roehm, III et al. | |
| 7,643,884 | B2 | 1/2010 | Pond, Jr. et al. | |
| 7,666,205 | B2 | 2/2010 | Weikel et al. | |
| 7,666,226 | B2 | 2/2010 | Schaller | |
| 7,666,227 | B2 | 2/2010 | Schaller | |
| 7,670,374 | B2 | 3/2010 | Schaller | |
| 7,670,375 | B2 | 3/2010 | Schaller | |
| 7,740,659 | B2 * | 6/2010 | Zarda | A61F 2/442 623/17.11 |
| 7,785,368 | B2 | 8/2010 | Schaller | |
| 7,918,874 | B2 | 4/2011 | Siegal | |
| 7,947,078 | B2 | 5/2011 | Siegal | |
| 7,955,391 | B2 | 6/2011 | Schaller | |
| 7,955,931 | B2 | 6/2011 | Appenzeller et al. | |
| 7,963,993 | B2 | 6/2011 | Schaller | |
| 7,967,864 | B2 | 6/2011 | Schaller | |
| 7,967,865 | B2 | 6/2011 | Schaller | |
| 8,007,535 | B2 | 8/2011 | Hudgins et al. | |
| 8,012,197 | B2 | 9/2011 | Bashiri et al. | |
| 8,057,544 | B2 | 11/2011 | Schaller | |
| 8,236,057 | B2 * | 8/2012 | Wirtel, III | A61F 2/441 623/17.12 |
| 8,460,383 | B2 | 6/2013 | Wirtel, III et al. | |
| 8,518,118 | B2 * | 8/2013 | Sack | A61F 2/442 623/17.11 |
| 9,358,120 | B2 | 6/2016 | Richter et al. | |
| 9,572,676 | B2 | 2/2017 | Teisen et al. | |
| 9,585,761 | B2 | 3/2017 | Teisen et al. | |
| 2002/0013601 | A1 | 1/2002 | Nobles et al. | |
| 2003/0018390 | A1 * | 1/2003 | Husson | A61B 17/3201 623/17.16 |
| 2004/0230309 | A1 * | 11/2004 | DiMauro | A61F 2/28 623/17.12 |
| 2005/0070900 | A1 | 3/2005 | Serhan et al. | |
| 2005/0278027 | A1 * | 12/2005 | Hyde, Jr. | A61F 2/442 623/17.12 |
| 2007/0055265 | A1 | 3/2007 | Schaller | |
| 2007/0055275 | A1 * | 3/2007 | Schaller | A61B 17/70 606/92 |
| 2007/0123986 | A1 | 5/2007 | Schaller | |
| 2007/0162136 | A1 | 7/2007 | O'Neil et al. | |
| 2007/0288095 | A1 | 12/2007 | Wirtel et al. | |
| 2008/0133012 | A1 * | 6/2008 | McGuckin | A61F 2/441 623/17.12 |
| 2008/0154272 | A1 * | 6/2008 | Schaller | A61B 17/1642 606/93 |
| 2008/0234687 | A1 | 9/2008 | Schaller et al. | |
| 2008/0234827 | A1 * | 9/2008 | Schaller | A61B 17/8852 623/17.16 |
| 2009/0088788 | A1 | 4/2009 | Mouw | |
| 2009/0118833 | A1 | 5/2009 | Hudgins et al. | |
| 2009/0182386 | A1 | 7/2009 | Schaller | |
| 2009/0222096 | A1 | 9/2009 | Trieu | |
| 2009/0234454 | A1 | 9/2009 | Siegal | |
| 2009/0234457 | A1 | 9/2009 | Lotz et al. | |
| 2009/0248159 | A1 | 10/2009 | Aflatoon | |
| 2009/0275913 | A1 | 11/2009 | Trieu | |
| 2010/0198263 | A1 | 8/2010 | Siegal et al. | |
| 2010/0234954 | A1 | 9/2010 | Justis et al. | |
| 2010/0241177 | A1 * | 9/2010 | Schaller | A61B 17/7094 606/86 A |
| 2010/0249505 | A1 | 9/2010 | Shoham et al. | |
| 2010/0262147 | A1 | 10/2010 | Siegal et al. | |
| 2010/0262242 | A1 | 10/2010 | Chavatte et al. | |
| 2011/0004307 | A1 | 1/2011 | Ahn et al. | |
| 2011/0046737 | A1 | 2/2011 | Teisen | |
| 2011/0066192 | A1 * | 3/2011 | Frasier | A61F 2/441 606/86 A |

(56) References Cited

U.S. PATENT DOCUMENTS

| | | | |
|---|---|---|---|
| 2011/0092859 | A1 | 4/2011 | Neubardt |
| 2011/0118789 | A1 | 5/2011 | Siegal |
| 2011/0137332 | A1 | 6/2011 | Sepetka et al. |
| 2011/0152683 | A1 | 6/2011 | Gerrans et al. |
| 2011/0153019 | A1 | 6/2011 | Siegal |
| 2011/0172710 | A1 | 7/2011 | Thommen et al. |
| 2011/0178523 | A1 | 7/2011 | Siegal et al. |
| 2011/0184515 | A1 | 7/2011 | Siegal |
| 2011/0202133 | A1 | 8/2011 | Siegal |
| 2011/0218494 | A1 | 9/2011 | Gerrans et al. |
| 2011/0230967 | A1 | 9/2011 | O'Halloran et al. |
| 2011/0245926 | A1* | 10/2011 | Kitchen ................ A61F 2/4465 623/17.16 |
| 2011/0264146 | A1 | 10/2011 | Siegal |
| 2011/0307063 | A1 | 12/2011 | Schaller |
| 2011/0307064 | A1 | 12/2011 | Schaller |
| 2012/0116399 | A1 | 5/2012 | Appenzeller et al. |
| 2012/0191125 | A1 | 7/2012 | Babkes et al. |
| 2012/0259215 | A1 | 10/2012 | Gerrans et al. |
| 2012/0259216 | A1 | 10/2012 | Gerrans et al. |
| 2014/0107789 | A1 | 4/2014 | Schaller et al. |
| 2014/0277464 | A1 | 9/2014 | Richter et al. |
| 2014/0277465 | A1 | 9/2014 | Teisen et al. |
| 2014/0277466 | A1 | 9/2014 | Teisen et al. |
| 2014/0277481 | A1* | 9/2014 | Lee ........................ A61F 2/4455 623/17.16 |
| 2017/0119535 | A1 | 5/2017 | Teisen et al. |

FOREIGN PATENT DOCUMENTS

| | | | | |
|---|---|---|---|---|
| WO | 03/059213 | A2 | 7/2003 | |
| WO | 2007/022194 | A2 | 2/2007 | |
| WO | 2007/076049 | A2 | 7/2007 | |
| WO | 2008/063435 | A1 | 5/2008 | |
| WO | 2008/103781 | A2 | 8/2008 | |
| WO | 2008/103832 | A2 | 8/2008 | |
| WO | WO 2008103832 | A2 * | 8/2008 | ......... A61B 17/8852 |
| WO | 2009/006432 | A2 | 1/2009 | |
| WO | 2013/023898 | A1 | 2/2013 | |

OTHER PUBLICATIONS

International Search Report for Application No. PCT/US2014/021236, dated Jun. 13, 2014 (7 Pages).

International Search Report for Application No. PCT/US2014/021266, dated Sep. 2, 2014 (9 Pages).

Written Opinion for Application No. PCT/US2014/021266, dated Sep. 2, 2014 (10 Pages).

* cited by examiner

EXPANDABLE COIL SPINAL IMPLANT

CROSS-REFERENCE TO RELATED APPLICATIONS

This application is a continuation of U.S. application Ser. No. 13/804,336, filed on Mar. 14, 2013, which is hereby incorporated by reference in its entirety.

FIELD

The disclosure relates generally to spinal implants, and in particular, to implants configured as an expandable coil with a balloon interspersed between or within the loops of the coil, which when inflated with a fluid expands the coil to facilitate spinal reconstruction, particularly when needed to correct lesions or diseases of the vertebral body, a disc, and at least one spinal motion segment, also known as a functional spinal unit.

BACKGROUND

In the spine, vertebrae provide the rigidity and support of the spinal column, and the intervertebral discs provide flexibility and shock absorption during movement. In some individuals, the intervertebral discs may be damaged from trauma, and/or may lose their integrity due to degeneration. Degenerated and damaged discs negatively affect the flexibility and load bearing capacity of the spine, and may cause pain and discomfort in subjects, and may inhibit the ability of the subject to move or lift objects.

To restore function of degenerated or damaged discs, such discs are typically surgically removed, at least in part, and replaced with a prosthetic disc. Prosthetic discs may take the form of an implant, which bridges adjacent vertebrae together and assumes the function of the natural disc. Such implants often include bone or a material that facilitates bone growth, in which case the implants support fusion of two adjacent vertebrae via new bone growth. There remains a need to provide implants for replacing intervertebral discs that re-establish and maintain a natural spinal alignment.

In some cases, bone tumors or significant bone trauma necessitate partial or entire removal of a vertebral body. There is also a need to provide implants that provide for a three dimensional reconstruction of vertebral bodies that restore lost height, fill cavities, and provide long term stabilization of the reconstructed vertebrae.

SUMMARY

The disclosure features spinal implants that may be used for vertebral body reconstruction and/or intervertebral disc replacement. In general, the implants comprise an expandable coil, and the coil comprises a top and bottom, and is formed from a hollow tube having a first end, a second end, and side walls that define a lumen. The first end and/or the second end may be open, or may be closed. The coil comprises a plurality of loops formed out of the hollow tube, and vertically adjacent loops have a space between their respective lower and upper sidewalls. The coil thus comprises a plurality of loops and a plurality of spaces.

In some aspects, the implants comprise a plurality of apertures through the sidewalls that extend into the lumen. In some aspects, the implants comprise, instead of a plurality of apertures, a gap through the sidewalls that extends into the lumen. The gap extends longitudinally from the first end to the second end, and is present on either an upper or lower surface of the tube that has been formed into loops.

The implants may comprise at least one balloon interspersed throughout and thereby occupying the space between vertically adjacent loops. In some aspects, the balloon is housed within the lumen until it is deployed. The balloon may be deployed from the lumen, through the gap, and into the space between vertically adjacent loops. When in the space between vertically adjacent loops, and when filled, the balloon pushes the loops of the coil apart in an upward and downward direction, thereby expanding the coil. For example, as it fills and expands to its outward capacity, the balloon pushes on the lower surface of the loop directly above the balloon, pushing that lower surface (and loop) upward, and the balloon also pushes on the upper surface of the loop directly below the balloon, pushing that upper surface (and loop) downward). When the coil is expanded, the implant has a height that approximates the height of an intervertebral disc and/or the height of a vertebral body, and in some aspects, approximates the height of two vertebrae and at least one disc (e.g., a spinal motion segment or functional spinal unit). In some aspects, a spinal motion segment comprises two adjacent vertebral bodies, the facet joint created by their articular processes, the intervertebral disc between them and associated soft tissue. The intervertebral disc and the facet joints (one on each side of the midline) allow for motion in flexion, extension, side bending and rotation at the level of the motion segment. The at least one balloon may be compliant, semi-compliant, or non-compliant.

The hollow tube may be comprised of a flexible metal, including a metal that has a shape memory capacity, enabling stress-induced superelasticity, and reversible deformation up to 8-10% strain. Suitable metals include titanium, steel, aluminum, or alloy such as nitinol.

A bone graft material or bone cement may be present in the lumen, or may be introduced into the lumen by way of a tool that is releasably connected to the first end, and is also operably connected to a supply of bone graft material or bone cement. Thus, the tool may take the bone graft material or bone cement from the supply and insert it into the lumen of the implant. The bone graft material may be cancellous autograft bone, allograft bone, demineralized bone matrix (DBM), bone morphogenic protein (BMP), or any combination thereof. The bone cement may comprise calcium phosphate or hydroxyapatite.

In some aspects, the implants comprise a plurality of balloons, including two, three, four, five, six, seven, eight, or more balloons. These balloons are interspersed through and occupy the space between each loop, including after such balloons are deployed from the lumen. Any of the balloons may comprises a single chamber, or a plurality of chambers. The balloons also comprise an opening that allows air or a fluid to pass into the chamber in order to fill the balloon. To the opening, a tool may be releasably connected, and this tool may also be operably connected to a supply of air or a fluid. A fluid to be inserted, including injected, into the balloons may comprise water, saline, a contrast medium, a hydrogel, or a bone cement. The fluid may be in a liquid form when inserted into the balloon chamber, and polymerizable, crystalizable, or capable of solidifying once inserted into the balloon and/or inside of the body upon implantation of the implant. The one or plurality of balloons may be affixed to the loops by way of an adhesive, though in some aspects an adhesive is not used.

The disclosure also features methods for augmenting or reconstructing a vertebral body, and methods for repairing or replacing an intervertebral disc, and methods for reconstructing a spinal motion segment. The methods generally comprise implanting the implant, such as any implant described or exemplified herein, into a vertebral body (e.g., a void in a vertical body produced by a corpectomy procedure whereby a portion of the vertebral bone is removed) or intervertebral space, or removed spinal motion segment, filling the balloon with an amount of a fluid sufficient to deploy the balloon from the lumen and/or expand the coil and increase the height of the implant to a desired height, optionally deploying a bone graft material or bone cement from the plurality of apertures or gap, and/or first and second openings into the vertebral body or intervertebral space, and optionally, removing the expandable coil from the vertebral body or intervertebral space. The coil may be removed from the vertebral body or intervertebral space after deploying the bone graft material or bone cement, in cases where a bone graft material or bone cement was deployed.

BRIEF DESCRIPTION OF THE DRAWINGS

The disclosure is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

The terms subject and patient are used interchangeably. A patient may be any animal, including mammals such as companion animals, laboratory animals, and non-human primates. Human beings are preferred.

The disclosure features devices, systems, and methods for replacing or reconstructing an intervertebral disc, or replacing or reconstructing at least a portion of a vertebrae such as a vertebral body, or replacing or reconstructing a spinal motion segment in a patient in need thereof. The devices, systems, and methods may find use, for example, in spinal reconstruction, repair, or fusion procedures. A foundational feature is an expandable coil with balloons interspersed throughout the spaces of the coil. Larger expandable coils may be used for reconstruction of vertebral bodies. Smaller expandable coils may be used in the intervertebral space for disc replacement. Even larger expandable coils may be used for reconstruction of spinal motion segments spanning at least two vertebral bodies and at least one intervertebral disc.

The components of the expandable coil can be fabricated from any suitable material or combination of materials. Materials include plastic, polymers, metals, and composites, preferably medical or surgical grade, and preferably biocompatible, as well as natural or synthetic bone. Non-limiting examples of suitable polymers include polyetheretherketone (PEEK), polyamineimide (PAI), polyethyleneimine (PEI), polyphenylsulfone (PPSU), polyoxymethylene (POM), and ultra high molecular weight polyethylene (UHMW-PE). Non-limiting examples of suitable metals include titanium, tantalum, aluminum, surgical-grade steel, as well as alloys, including titanium alloys such as nitinol (nickel-titanium alloy), Ti-6Al-4V (TAV), and Ti-6Al-7Nb (TAN), and cobalt-chromium alloys. Nitinol is preferred. Carbon may also be used to fabricate at least part of the implant coil. Preferably, the material is sufficiently flexible so that the coil may expand.

Figure 1A:
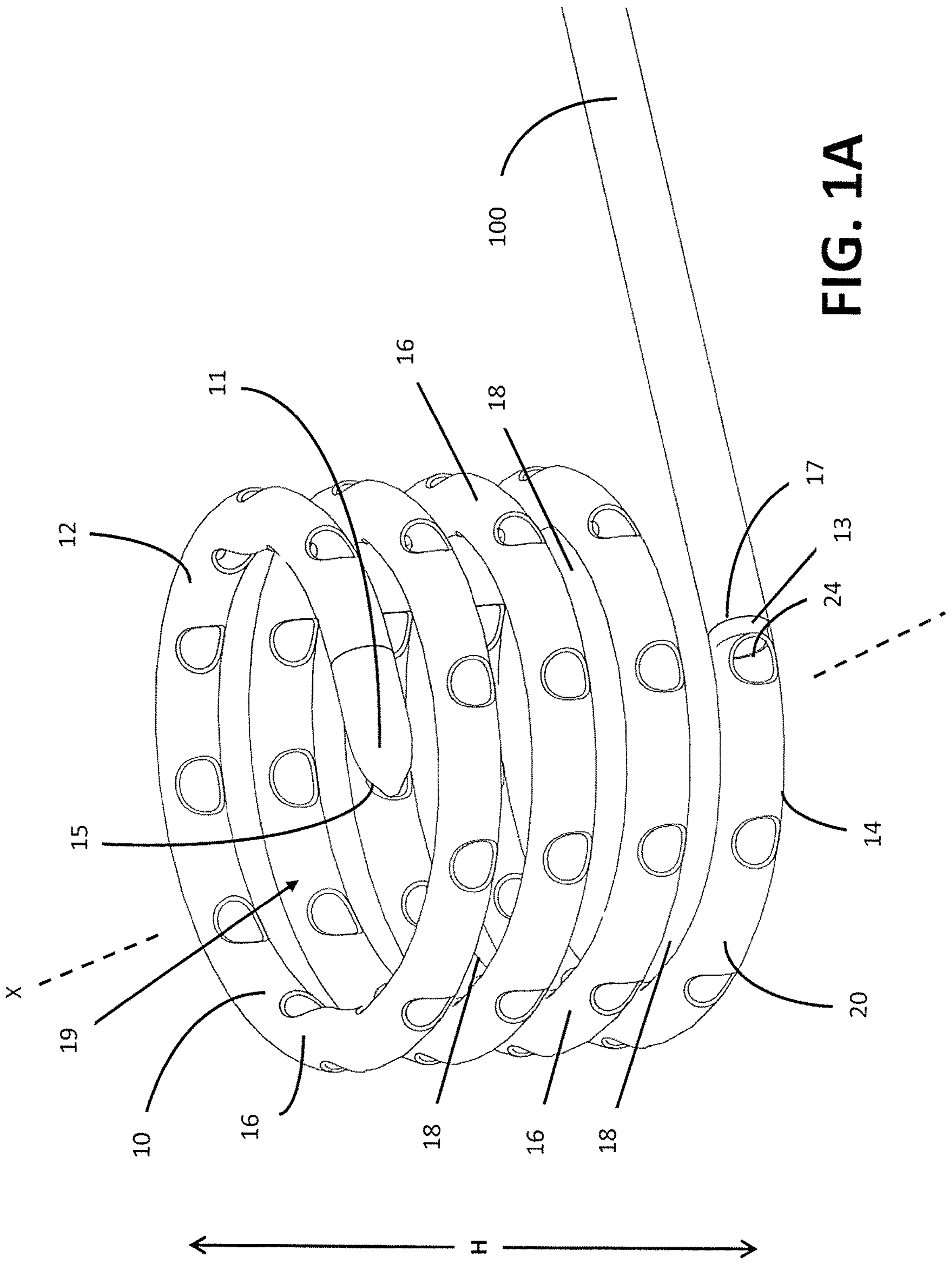
FIG. 1A and FIG. 1B each show a perspective view of an embodiment of a coiled spinal implant without a balloon interspersed between the coil loops.
Figure 1B:
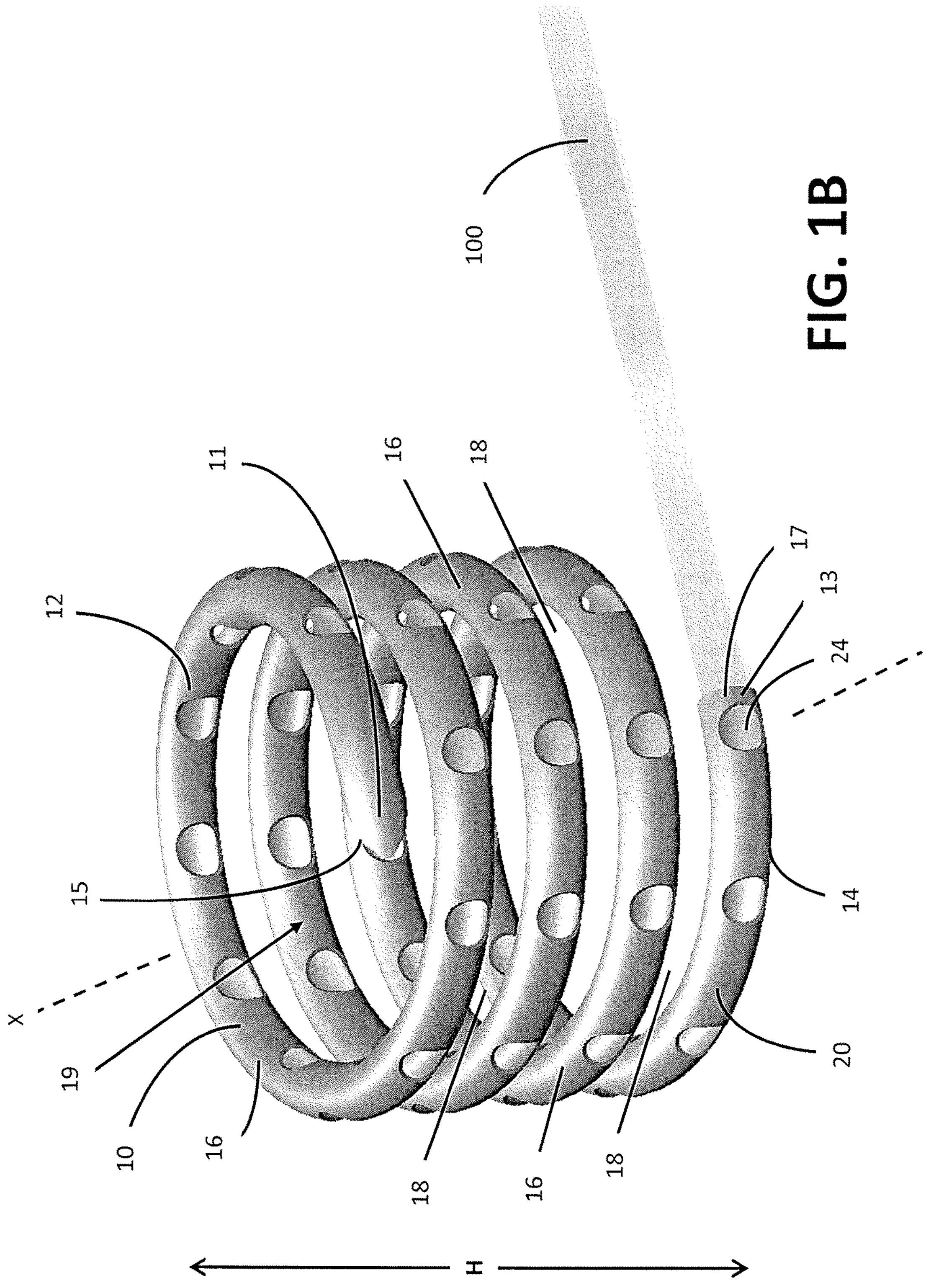

Referring now to the drawings, in which like reference numbers refer to like elements throughout the various figures that comprise the drawings, FIG. 1 shows an example of an expandable coil implant 10. The coiled implant 10 comprises a top 12 and a bottom 14, and a plurality of expandable loops 16. As the implant 10 is a coil, the coiled implant 10 also includes a plurality of spaces 18 that are interspersed between the loops 16. The spaces 18 are vertically oriented between adjacent loops 16. For example, each loop 16 comprises a sidewall 20 that has an upper, lower, outer, and inner surface, and each space 18 is located directly beneath the lower surface of a loop 16 and directly above an upper surface of the loop 16 that is closest to the upper loop 16 in a vertical plane. The spaces 18 are between vertically adjacent loops, not between horizontally adjacent loops; a central void 19 is between horizontally adjacent loops. The coiled implant 10 comprises a first end 11, generally located at the top 12, and a second end 13, generally located at the bottom 14. The first end 11 and second end 13 may comprise a point, or may be flat, and they each are preferably blunt. The first end 11 and second end 13 may comprise an edge, barb, or projection that engages and digs into vertebral bone, for example, to help hold the implant 10 in place.

Figure 5A:
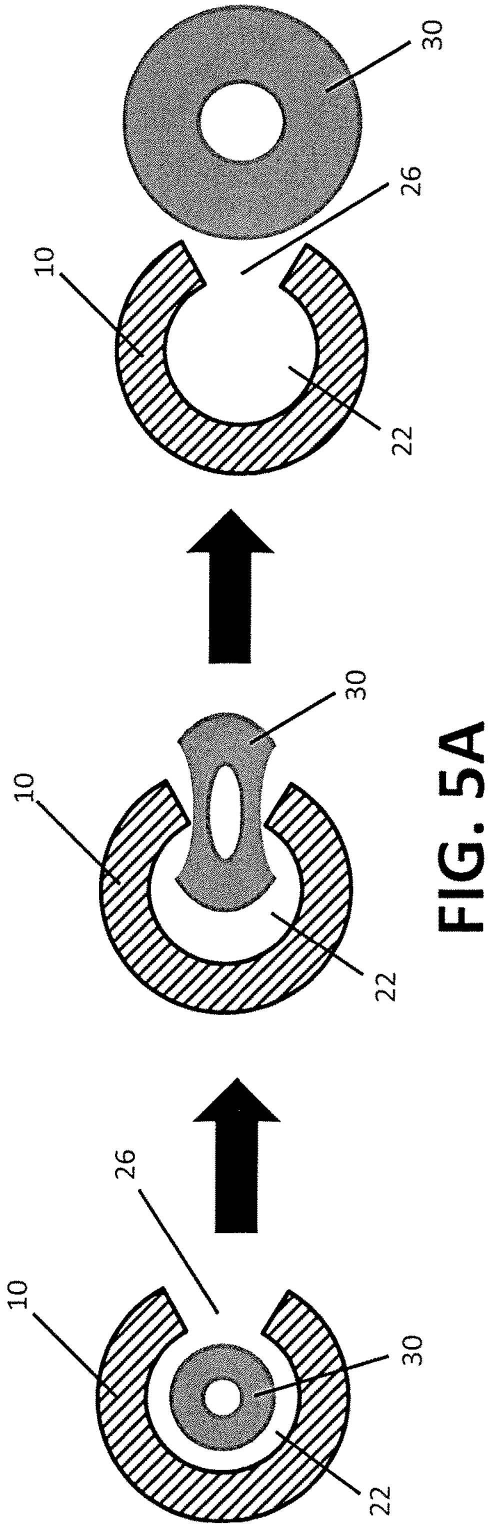
FIG. 5A shows a cross-sectional representation of the deployment of a balloon out of the lumen of a loop of the coil, with the gap in the sidewall being relatively narrow.
Figure 5B:
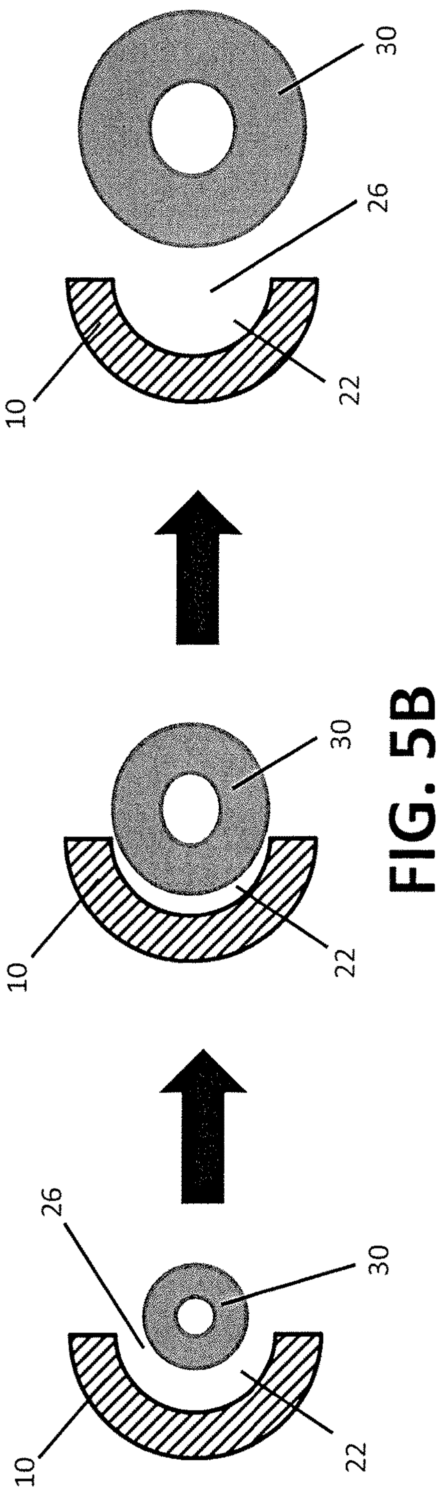
FIG. 5B shows a cross-sectional representation of the deployment of a balloon out of the lumen of a loop of the coil, with the gap in the sidewall being relatively large, approximating a half pipe; and, FIG. 6 shows a close-up of a the deployment of a balloon out of the lumen of a loop of the coil, with the gap in the sidewall aiming downward toward the upper surface of an adjacent loop.

The coiled implant 10 loops 16 are preferably hollow, and thus comprise tube-shaped sidewalls 20 that surround a lumen 22 (FIG. 5*a* and FIG. 5B). The tube-shaped sidewalls 20 may comprise a substantially round, elliptical, quadrilateral, pentagonal, hexagonal, heptagonal, or octagonal shape, though a shape with any number of sides may be employed. FIG. 1 shows the sidewalls 20 in a substantially round shape. In some aspects, the implant 10 may also include a plurality of apertures 24 that pass through the sidewalls 20 and into the lumen 22. In addition, in some aspects, at least one of the first end 11 and the second end 13 may comprise an opening 15, 17.

A first tool 100 may releasably engage either or both of the first end 11 or second end 13 of the implant 10. The first tool 100 may comprise a catch or snare, or simply be compatibly shaped to fit over or into the opening 15 or 17, including with a friction fit. The first tool 100 may comprise a pump, and or may be operably connected to a supply of bone graft material, and/or to a supply of air or fluid.

Figure 6:
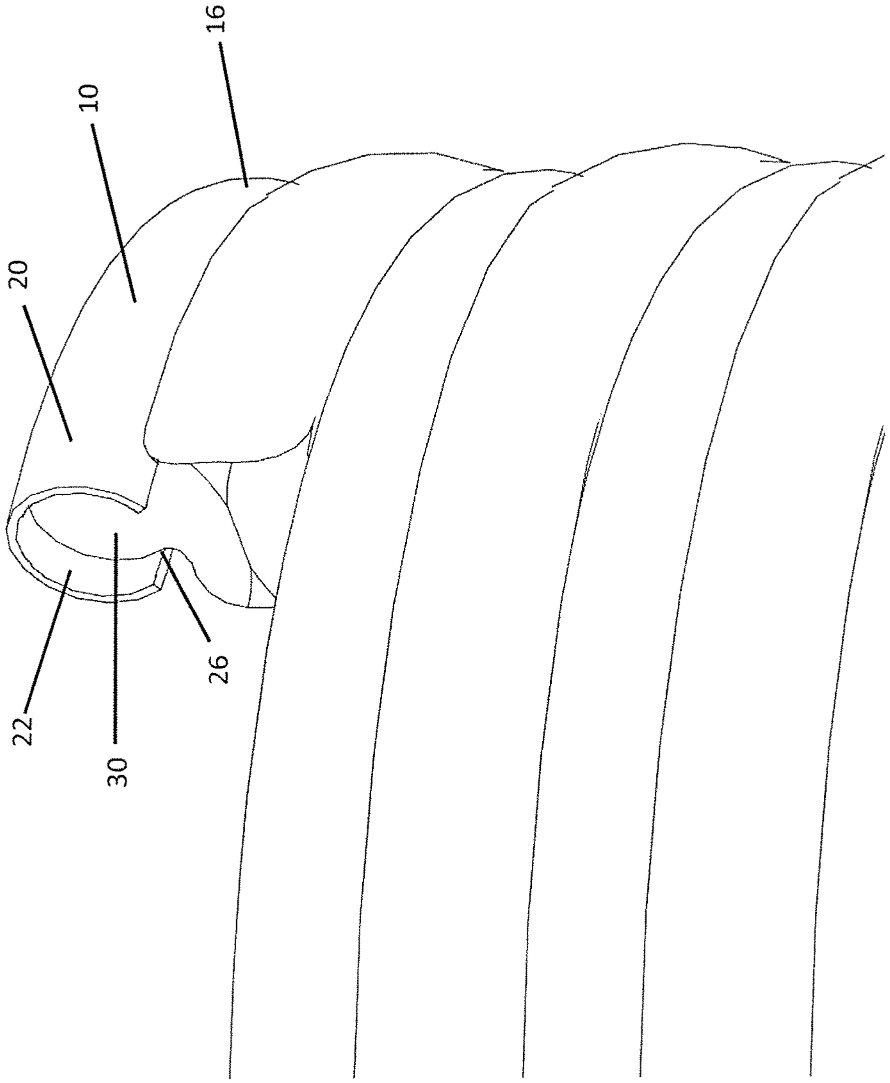

In some aspects, the implant 10 does not include a plurality of apertures 24 through the sidewalls 20. Instead, in such aspects, the sidewalls 20 comprise a gap 26 through the sidewalls 20 and into the lumen 22. The gap 26 runs substantially the entire length of the implant 10, for example, the gap extends from the first end 11 to the second end 13. The gap 26 may be on any of the upper, lower, outer, or inner surface of the sidewalls 20 of the loops 16. Preferably, the gap 26 is on either the upper surface or lower surface of the sidewalls 20. FIG. 6 shows an example of the gap 26 on the lower surface of the sidewalls 20.

Figure 2A:
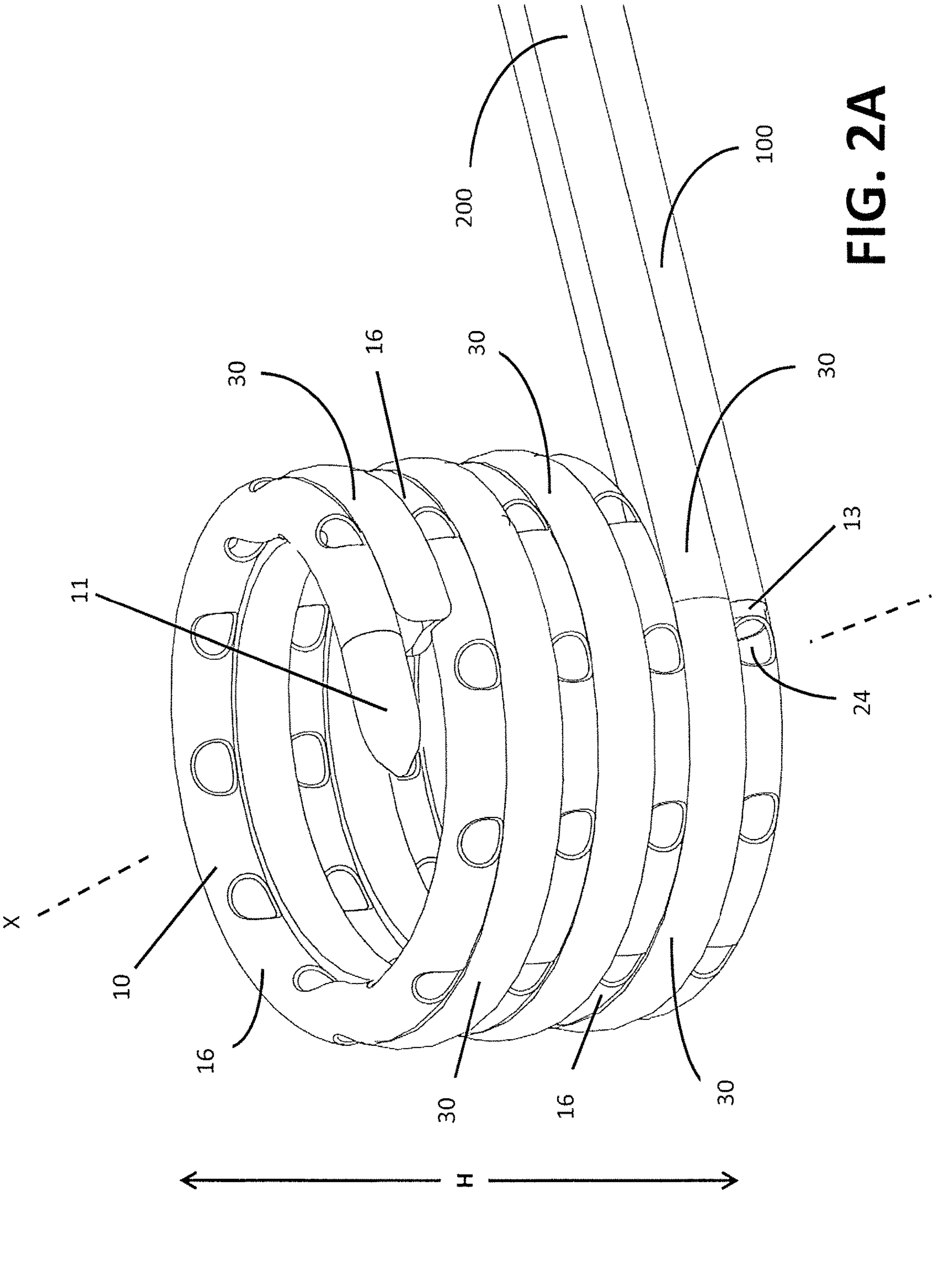
FIG. 2A and FIG. 2B each show a perspective view of an embodiment of a coiled spinal implant with a balloon interspersed between the coil loops.
Figure 2B:
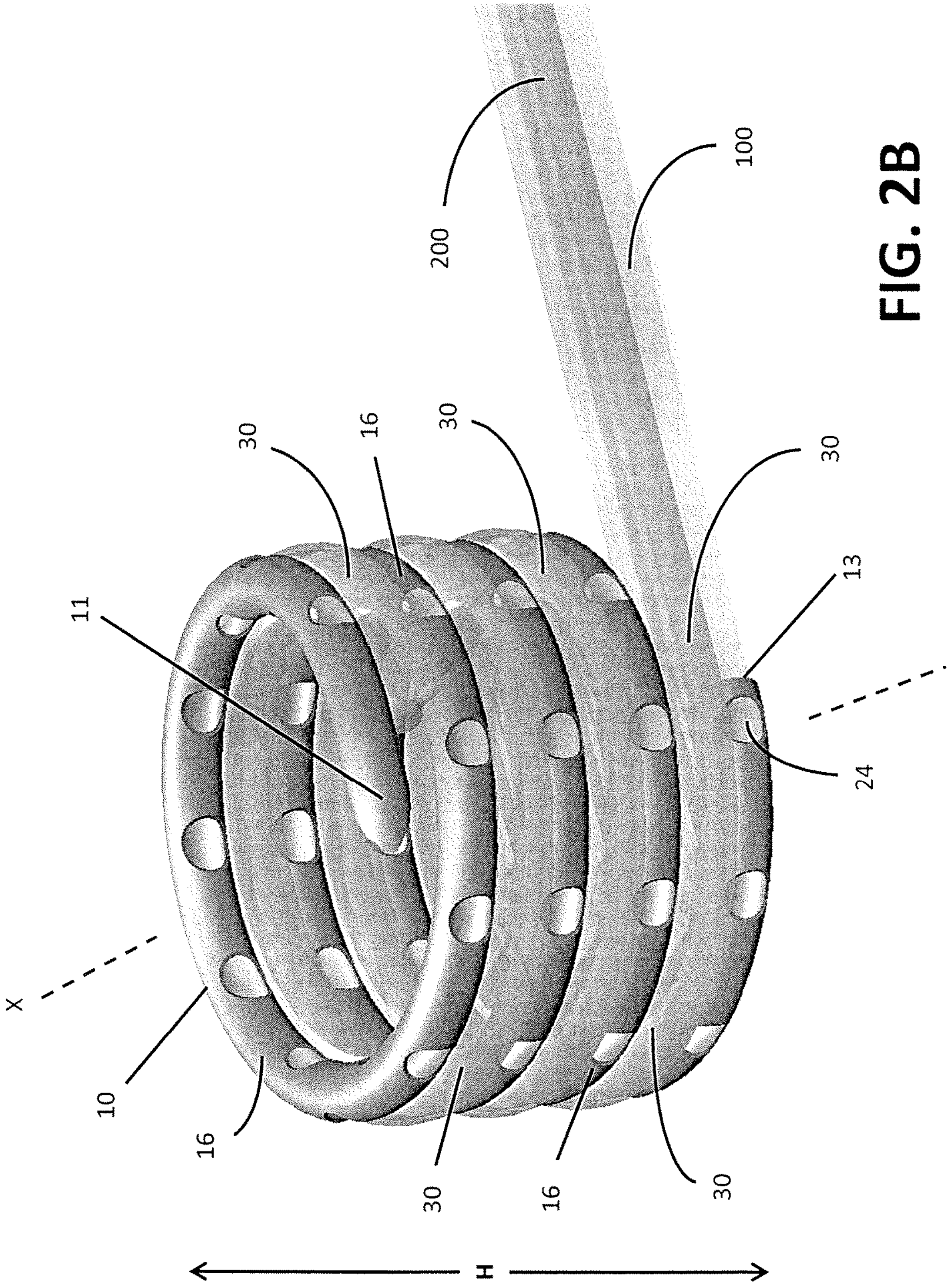

In some aspects, the spaces 18 between the loops 16 are preferably occupied by a balloon 30 or membrane 30. An example of this embodiment is shown in FIG. 2. The balloon 30 or membrane 30 may be wedged between the sidewalls 20 of vertically adjacent loops 16, for example, with a friction fit, and/or may be affixed to the sidewalls 20 by way of an adhesive.

In some aspects, the balloon 30 or membrane 30 is not present in the spaces 18 at first, for example, during the implantation process itself. In such aspects, the balloon 30 or membrane 30 is housed within the lumen 22 of the implant 10, and is deployed from the lumen 22 into the spaces 18 once the implant 10 is placed in the desired location within the vertebrae or intervertebral space. While housed within the lumen 22, the balloon 30 or membrane 30 is preferably substantially not inflated. In such aspects, the implant 10 comprises the gap 26, and the balloon 30 or membrane 30 is deployed from the lumen 22, through the gap 26, and into the spaces 18 of the implant 10. See, e.g., FIG. 6. The gap 26 may comprise any suitable width. See, e.g., FIGS. 5A and 5B. The balloon 30 or membrane 30 may be deployed, for example, by filling it with air or a fluid as described herein. The filling of the balloon 30 or membrane 30 forces it through the gap 26, where it continues to be filled, becomes wedged within the spaces 18 and thereby contacts the upper and lower surfaces of vertically adjacent loops 16, and as it continues to be filled, forces vertically adjacent loops 16 upward and downward, respectively, thereby expanding the coil.

A second tool 200 may releasably engage an open end of the balloon 30 or membrane 30, whether the balloon 30 or membrane 30 is within the lumen 22 and/or in the spaces 18 and/or in the central void 19. The second tool 200 may comprise a tube, including a flexible plastic or rubber tube, or even a more rigid metal tube. For example, such a tube may engage an opening on the balloon 30 or membrane 30, including with a friction fit. The second tool 200 may comprise a pump, and or may be operably connected to a supply of air or fluid.

The first tool 100 may be used to hold the implant 10, for example, to place the coiled implant 10 at its desired location within the vertebral body or in the intervertebral space. The first tool 100 may also be used to move the implant 10 in order to position the implant 10 at its desired location. In some aspects, the first tool 100 may be used to deliver a bone graft material or bone cement through the first end 11 or second end 13 and into the lumen 22 of the implant 10. For example, the a bone graft material may be extruded through the first tool 100 and through the opening 15 or 17

(depending on if the first tool 100 is attached to the first end 11 or second end 13) of the coiled implant 10 to which the first tool 100 is attached. The bone graft material or bone cement may then pass into and through the lumen 22, and may exit the lumen 22 through the plurality of apertures 24, or the gap 26, as well as the opening 15 or 17 that is not connected to the first tool 100. Thus, the plurality of apertures 24 and the openings 15 or 17 deploy the bone graft material or bone cement. In some aspects, the gap 26 may be used to deploy the bone graft material or bone cement.

More than one balloon 30 or membrane 30 may be used. The balloon 30 or membrane 30 may be fabricated from any suitable material. For example, the material may comprise a biocompatible plastic, polymer, rubber, composite, foil, or combination thereof. The balloon 30 or membrane 30 may be compliant or semi-compliant, for example, may expand upon filling. The balloon 30 or membrane 30 may be non-compliant, for example, may not substantially expand upon filling, although such non-compliant balloons 30 or membranes 30 may unfold if folded up. The balloon 30 or membrane 30 may comprise a single volume or a plurality of volumes, for example, in the latter case, the balloon 30 or membrane 30 may have a plurality of chambers that may be filled. The balloon 30 or membrane 30 includes at least one opening in communication with each chamber through with fluid or air may be inserted in order to fill the chamber. Once the balloon 30 or membrane 30 is filled to a desired level, the opening may be closed, for example, with a stopper, tie, adhesive, seal, solder, or other suitable closure. The opening may comprise a valve, including a self-sealing valve.

The balloon 30 or membrane 30 may be filled, for example, with suitable amount of air or a fluid. For example, the balloon 30 or membrane 30 may be at least partially filled with air or a fluid such that the balloon 30 or membrane 30 expands, thereby holding the balloon 30 or membrane 30 in place in the inter-loop spaces 18 during insertion and placement of the implant 10. Once the implant 10 is seated in the desired location within the vertebral body or the intervertebral space, the balloon 30 or membrane 30 may be filled with additional air or liquid to further expand the balloon 30 or membrane 30. As the balloon 30 or membrane 30 is filled and expands, it exerts outward pressure on adjacent loops 16 of the coil, and thereby forces the loops 16 apart from each other in an upward/downward direction about an axis X. As the loops 16 expand apart, the height H of the implant 10 increases. Increasing the height H of the implant 10 enhances the fit of the implant 10 between vertebrae, and when used as a disc replacement in the intervertebral space, establishes the desired distance between the endplates of adjacent vertebrae, for example, to restore the natural distance formerly occupied by the natural disc, or to establish an angle of lordosis.

Together, the balloon 30 or membrane 30 and the loops 16 may essentially "wall off" a center 19 of the implant 10, the center 19 being essentially a void 19 surrounded by the loops 16 and spaces 18, which spaces 18 may be occupied by a balloon 30 or membrane 30. Thus, in some aspects, a bone graft material, for example, such a material deployed through the apertures 24 and/or openings 15 or 17, may fill the void 19, being contained between the inner surface of the loops 16 and inner surface of the balloon 30 or membrane, and may make contact vertebral bone, and in some aspects, contact bone of adjacent vertebrae.

In some alternative embodiments, the balloon 30 or membrane 30 also is present in at least a portion of the void 19 in the center of the coil. Thus, the balloon 30 or membrane 30 may occupy some or all of the center 19 of the coiled implant 10. Such a balloon 30 or membrane 30 may also be in at least one of the spaces 18 between the loops 16, or the balloon 30 or membrane 30 may not occupy any of the spaces 18 between the loops 16, and essentially be caged by the plurality of loops 16 that constitute the coil.

The bone graft material may be natural or synthetic, and may comprise cancellous autograft bone, allograft bone, collagen-hydroxyapatite, demineralized bone matrix (DBM), porous synthetic bone graft substitute, bone morphogenic protein (BMP), or combinations thereof. Any material that promotes bone growth and osseointegration may be used. The bone graft material may be in the form of a paste, putty, or slurry. The bone graft material may comprise growth factors. Numerous bone graft materials are commercially available, and are suitable for use in connection with the implant 10.

The balloon 30 or membrane 30 may be filled by way of the second tool 200, which may be attached to the open end of the balloon 30 or membrane, and which thereby may deliver the air or fluid into the balloon 30 or membrane 30 chamber. The fluid may comprise a physiologic saline solution, a radiopaque contrast solution, or may comprise water, or may comprise a hydrogel, or may comprise a polymerizable monomer or polymer, or may comprise a bone cement, or may comprise a crystalizable material. Non-limiting examples of a bone cement comprise calcium phosphate (CaP) and/or comprise hydroxyapatite. Preferably, the fluid is biocompatible. Preferably, the fluid provides for a cushioning effect, yet may bear some of the load forces from movement of the spine, for example, when the subject moves, or lifts objects. For vertebral reconstruction, the fluid may be a bone cement, and provide less of a cushioning effect and provides more of a load bearing function. The fluid may comprise polymethyl methacrylate (PMMA). The fluid may be in a liquid form when inserted into the balloon chamber polymerizable, crystalizable, or capable of solidifying once inserted into the balloon and/or inside of the body upon implantation of the implant.

The coiled implant 10 comprises a height H (FIG. 1 and FIG. 2). The implant height H, expanded or unexpanded, is preferably measured from the surface of the top 12 to the surface of the bottom 14. Coiled implants 10 for vertebral reconstruction may have comparatively larger heights H, which substantially approximate the height of the vertebral body being reconstructed. Coiled implants 10 for disc replacement may have comparatively smaller heights H, which substantially approximate the height of the disc being replaced.

The height H of the non-expanded coiled implant 10 that is used for disc replacement (e.g., an intervertebral coiled implant 10) may be about 5 mm to about 20 mm. In some aspects, the height H of the non-expanded disc replacement implant is about 5 mm to about 10 mm, about 5 mm to about 12 mm, about 5 mm to about 14 mm, about 5 mm to about 15 mm, about 5 mm to about 16 mm, about 5 mm to about 18 mm, about 5 mm to about 20 mm, about 7 mm to about 10 mm, about 7 mm to about 12 mm, about 7 mm to about 14 mm, about 7 mm to about 15 mm, about 7 mm to about 16 mm, about 7 mm to about 18 mm, about 7 mm to about 20 mm, about 9 mm to about 12 mm, about 9 mm to about 14 mm, about 9 mm to about 15 mm, about 9 mm to about 16 mm, about 9 mm to about 18 mm, about 9 mm to about 20 mm, about 10 mm to about 12 mm, about 10 mm to about 14 mm, about 10 mm to about 15 mm, about 10 mm to about 16 mm, about 10 mm to about 18 mm, about 10 mm to about 20 mm, about 11 mm to about 13 mm, about 12 mm to about 14 mm, about 12 mm to about 15 mm, about 12 mm to about 16 mm, about 12 mm to about 18 mm, about 12 mm to about 20 mm, about 13 mm to about 15 mm, about 14 mm to about 16 mm, about 14 mm to about 18 mm, about 14 mm to about 20 mm, about 15 mm to about 17 mm, about 15 mm to about 18 mm, or about 15 mm to about 20 mm. The unexpanded implant height may be less than 5 mm, or greater than 20 mm.

The expanded implant 10 may approximate the height of the intervertebral disc being replaced, including a cervical, thoracic, lumbar, or sacral disc. Once expanded, the height H of the coiled implant 10 used for disc replacement may be about 5 mm to about 35 mm. In some aspects, the height H of the expanded implant is about 7.5 mm to about 10 mm, about 7.5 mm to about 12 mm, about 7.5 mm to about 14 mm, about 7.5 mm to about 15 mm, about 7.5 mm to about 16 mm, about 7.5 mm to about 18 mm, about 7.5 mm to about 20 mm, about 7.5 mm to about 25 mm, about 7.5 mm to about 27 mm, about 7.5 mm to about 30 mm, about 9 mm to about 12 mm, about 9 mm to about 15 mm, about 8 mm to about 16 mm, about 8 mm to about 18 mm, about 8 mm to about 20 mm, about 9 mm to about 22 mm, about 9 mm to about 24 mm, about 9 mm to about 25 mm, about 9 mm to about 30 mm, about 10 mm to about 12 mm, about 10 mm to about 14 mm, about 10 mm to about 15 mm, about 10 mm to about 16 mm, about 10 mm to about 18 mm, about 10 mm to about 20 mm, about 10 mm to about 22 mm, about 10 mm to about 24 mm, about 10 mm to about 26 mm, about 10 mm to about 28 mm, about 10 mm to about 30 mm, about 12 mm to about 16 mm, about 12 mm to about 18 mm, about 12 mm to about 20 mm, about 12 mm to about 22 mm, about 12 mm to about 24 mm, about 12 mm to about 26 mm, about 12 mm to about 30 mm, about 14 mm to about 18 mm, about 14 mm to about 20 mm, about 14 mm to about 22 mm, about 14 mm to about 24 mm, about 16 mm to about 18 mm, about 16 mm to about 20 mm, about 16 mm to about 22 mm, about 16 mm to about 24 mm, about 18 mm to about 20 mm, about 18 mm to about 22 mm, about 18 mm to about 25 mm, about 20 mm to about 22 mm, about 20 mm to about 24 mm, about 22 mm to about 26 mm, or about 23 mm to about 25. The unexpanded implant height may be less than 5 mm, or greater than 35 mm.

The height H of the non-expanded coiled implant 10 that is used for vertebral body or spinal motion segment reconstruction (e.g., a vertebral body coiled implant 10) may be about 10 mm to about 60 mm. In some aspects, the height H may be about 10 mm to about 15 mm, about 10 mm to about 20 mm, about 10 mm to about 25 mm, about 10 mm to about 30 mm, about 10 mm to about 35 mm, about 10 mm to about 40 mm, about 10 mm to about 45 mm, about 15 mm to about 20 mm, about 15 mm to about 25 mm, about 15 mm to about 30 mm, about 15 mm to about 35 mm, about 15 mm to about 40 mm, about 15 mm to about 45 mm, about 20 mm to about 25 mm, about 20 mm to about 30 mm, about 20 mm to about 35 mm, about 20 mm to about 40 mm, about 20 mm to about 45 mm, about 25 mm to about 30 mm, about 25 mm to about 35 mm, about 25 mm to about 40 mm, about 25 mm to about 45 mm, about 30 mm to about 40 mm, about 30 mm to about 45 mm, or about 35 mm to about 40 mm.

The expanded implant 10 may approximate the height of the vertebral body or spinal motion segment being reconstructed, including a cervical, thoracic, lumbar, or sacral vertebral body, and in some aspects, also at least one intervertebral disc. Once expanded, the height H of the coiled implant 10 used for vertebral body reconstruction may be about 10 mm to about 80 mm. In some aspects, the expanded height H may be about 10 mm to about 15 mm, about 10 mm to about 20 mm, about 10 mm to about 25 mm, about 10 mm to about 30 mm, about 10 mm to about 35 mm, about 10 mm to about 40 mm, about 10 mm to about 45 mm, about 10 mm to about 50 mm, about 10 mm to about 55 mm, about 10 mm to about 60 mm, about 10 mm to about 70 mm, about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 15 mm to about 55 mm, about 15 mm to about 60 mm, about 15 mm to about 70 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 20 mm to about 55 mm, about 20 mm to about 60 mm, about 20 mm to about 65, mm about 25 mm to about 30 mm, about 25 mm to about 35 mm, about 25 mm to about 40 mm, about 25 mm to about 45 mm, about 25 mm to about 50 mm, about 25 mm to about 55 mm, about 30 mm to about 40 mm, about 30 mm to about 45 mm, about 30 mm to about 50 mm, about 30 mm to about 45 mm, about 35 mm to about 40 mm, about 35 mm to about 45 mm, about 35 mm to about 50 mm, or about 35 mm to about 60 mm.

Once the balloon 30 or membrane 30 is filled, the implant height H may increase up to about 100%, or in some aspects, up to about 125%, up to about 150%, or up to about 175%. Preferably, the implant height H increases about 10% to about 50% relative to the unexpanded height H. The implant height H may increase about 10% to about 40%, about 10% to about 33%, about 10% to about 30%, about 10% to about 25%, about 10% to about 20%, about 10% to about 15%, about 15% to about 45%, about 15% to about 40%, about 15% to about 33%, about 15% to about 30%, about 15% to about 25%, about 15% to about 20%, about 20% to about 50%, about 20% to about 40%, about 20% to about 33%, about 20% to about 30%, about 20% to about 25%, about 25% to about 50%, about 25% to about 40%, about 25% to about 33%, about 25% to about 30%, about 50% to about 05%, about 30% to about 40%, or about 40% to about 50%, relative to the unexpanded height H. In some aspects, the implant height H increases about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more, relative to its unexpanded height H.

In some aspects, the coiled implant 10 comprises a lordotic angle such that the height H on one side of the implant 10 is greater than the height H on an opposing side of the implant 10. The greater height H and the lesser height H may independently comprise a size described or exemplified herein.

The coiled implant 10 preferably has a substantially uniform width W. The width may be measured from the outer surface of a loop 16 on one side of the implant 10 to the outer surface of a loop 16 on the opposing side of the implant 10. In embodiments where the coiled implant 10 comprises a substantially circular shape, the width W comprises a diameter. The coiled implant may comprise non-circular shapes, including oval shapes or elliptical shapes, or even irregular shapes.

The implant width W may be about 10 mm to about 70 mm. In some aspects, the width W may be about 10 mm to about 20 mm, about 10 mm to about 25 mm, about 10 mm to about 30 mm, about 10 mm to about 35 mm, about 10 mm to about 40 mm, about 10 mm to about 45 mm, about 10 mm to about 50 mm, about 10 mm to about 65 mm, about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 15 mm to about 55 mm, about 15 mm to about 60 mm, about 15 mm to about 65 mm, about 15 mm to about 70 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 20 mm to about 60 mm, about 20 mm to about 65 mm, about 20 mm to about 70 mm, about 25 mm to about 30 mm, about 25 mm to about 35 mm, about 25 mm to about 40 mm, about 25 mm to about 45 mm, about 25 mm to about 50 mm, about 25 mm to about 60 mm, about 30 mm to about 35 mm, about 30 mm to about 40 mm, about 30 mm to about 45 mm, about 30 mm to about 50 mm, about 30 mm to about 60 mm, about 35 mm to about 40 mm, about 35 mm to about 45 mm, about 35 mm to about 50 mm, about 35 mm to about 55 mm, about 40 mm to about 45 mm, about 40 mm to about 50 mm, about 40 mm to about 55 mm, about 45 mm to about 50 mm, about 45 mm to about 55 mm, or about 45 mm to about 60 mm. Widths W shorter than 10 mm or longer than 70 mm are possible. It is preferred that the width W does not extend beyond the outer dimensions of the vertebrae.

In some aspects, the coiled implant 10 is preferably used for insertion into the intervertebral space. Thus, once inserted, the top 12 and bottom 14 of the implant 10 contact adjacent vertebral endplate bone, with the implant 10 seated between these adjacent vertebral endplates, in the space formerly occupied by a damaged, diseased, or degenerated disc. The coiled implant 10 may be inserted into the intervertebral space of cervical, thoracic, lumbar, or sacral vertebrae, and the height H may be according to the intended location of the implant within the spinal column (e.g., cervical, thoracic, lumbar, or sacral region of the spine).

In some aspects, the coiled implant 10 is preferably used for three dimensional reconstruction of a vertebral body. Thus, once inserted, the top 12 and bottom 14 of the implant 10 approximate the missing portion of the vertebral body, with the implant 10 preferably seated within a vertebral body, in the space formerly occupied by a damaged, diseased, or degenerated segment of the vertebral bone. The coiled implant 10 may be inserted into a cervical, thoracic, lumbar, or sacral vertebrae, and the height H may be according to the missing section of bone.

In some aspects, the coiled implant 10 is preferably used for three dimensional reconstruction of a spinal motion segment. Thus, once inserted, the top 12 and bottom 14 of the implant 10 approximate the missing portion of two vertebral bodies and at least one intervertebral disc, with the implant 10 preferably seated within in the space formerly occupied by a damaged, diseased, or degenerated segment of the vertebral bone and disc. The coiled implant 10 may be inserted into the space of a cervical, thoracic, lumbar, or sacral vertebrae, and their respective intervertebral disc, and the height H may be according to the missing section of bone and disc.

The implant 10 may be inserted into the body as part of spinal fusion procedure, or may be inserted as a form of a disc prosthesis without participating in any fusion. In this latter case, for example, the implant 10 occupies the intervertebral space, but does not facilitate new bone growth or fusion of adjacent vertebrae. If not fused, the implant 10 may be removed from the intervertebral space at some point in the future. When used as part of a spinal fusion procedure, the implant 10 includes bone graft material delivery, and it is this bone graft material that facilitates new bone growth and osseointegration of the implant 10.

In some preferred aspects, the material of which the implant 10 sidewalls 20 are fabricated has elasticity and also comprises a shape memory. For example, the material may be used to form a coil outside of the body of the subject, and the coil may be straightened for insertion into the subject, for example, to minimize the size of the incision through which the implant passes during the insertion procedure, yet the straightened coil returns to the coil shape once inserted into the body. A guide wire, including a flexible wire, may be used to guide the uncoiled implant 10 to its location in the disc space or in the vertebral body, and removed one the implant 10 is in a desired place, with removal of the guide wire allowing the coil to reform according to the shape memory of the material from which the coiled implant 10 is made.

In some aspects, the implant 10 comprises a temperature memory, e.g., thermal memory. For example, an implant 10 with a thermal memory may be straightened at room temperature, yet coiled at a heated temperature, including body temperature. In some aspects, the implant 10 comprises a super-elastic memory. For example, a straight tube (e.g., nitinol) may be pre-formed into a coil at high temperatures (e.g., 480-520° C.) and quenched, for example, in cooled water. The coiled tube may be forcibly uncoiled and inserted into/constrained by a straight cannula or sheath, yet when released from the straight cannula or sheath, the tube automatically re-coils, stemming from the super-elastic memory of the material from which the tube was fabricated.

The implant 10, whether in coiled form or in straightened form (including a guide wire, if used), may be inserted into the body of a subject through an anterior or posterior surgical procedure. The implant 10 may be inserted through the anterior, posterior, lateral side, or foramin of the vertebrae. The implant 10 may be inserted trans-pedicularly.

During a disc replacement procedure, at least a portion of the damaged or degenerated intervertebral disc is removed; the entire disc may be removed in some aspects. The intervertebral disc space may then be shaped and prepared to receive the coiled implant 10, including shaping and preparation of vertebral endplate bone, if necessary. Once the intervertebral space is ready, at least one coiled implant 10 may be inserted into the prepared intervertebral space. The coiled implant 10 may be inserted into the body as an uncoiled straight tube, for example, by housing the uncoiled implant 10 through a straight cannula, with the cannula inserted into the body. The implant 10 may then be released from the cannula, upon which the implant 10 will re-coil. The re-coiling may be due to the thermal memory or super-elastic memory of the material used to fabricate the implant 10.

During a vertebral body reconstruction procedure, at least a portion of the damaged or diseased vertebral body is removed (e.g., copectomy); the entire vertebral body may be removed in some aspects. The portion of the vertebral body may then be shaped and prepared to receive the coiled implant 10. Once the intervertebral space is ready, at least one coiled implant 10 may be inserted into the prepared portion of the vertebral body. The coiled implant 10 may be inserted into the body as an uncoiled straight tube, for example, by housing the uncoiled implant 10 through a straight cannula, with the cannula inserted into the body. The implant 10 may then be released from the cannula, upon which the implant 10 will re-coil. The re-coiling may be due to the thermal memory or super-elastic memory of the material used to fabricate the implant 10.

Preparation of the vertebral area for insertion of the implant 10 may comprise a cavity creation procedure. In such a procedure, the practitioner forms a cavity around the local area surrounding the target loci of the insert, for example, by pushing apart cancellous bone using a cavity forming balloon (which is not the balloon 30 of the implant 10). Once the cavity is formed, the cavity forming balloon may be deflated and removed, leaving behind an enlarged space or cavity. This cavity reduces resistance that may accompany insertion of the implant 10, including insertion via a cannula. In fact, the cavity may be used to allow the straightened implant 10 to re-coil within the cavity according to its thermal or super-elastic memory.

Figure 3A:
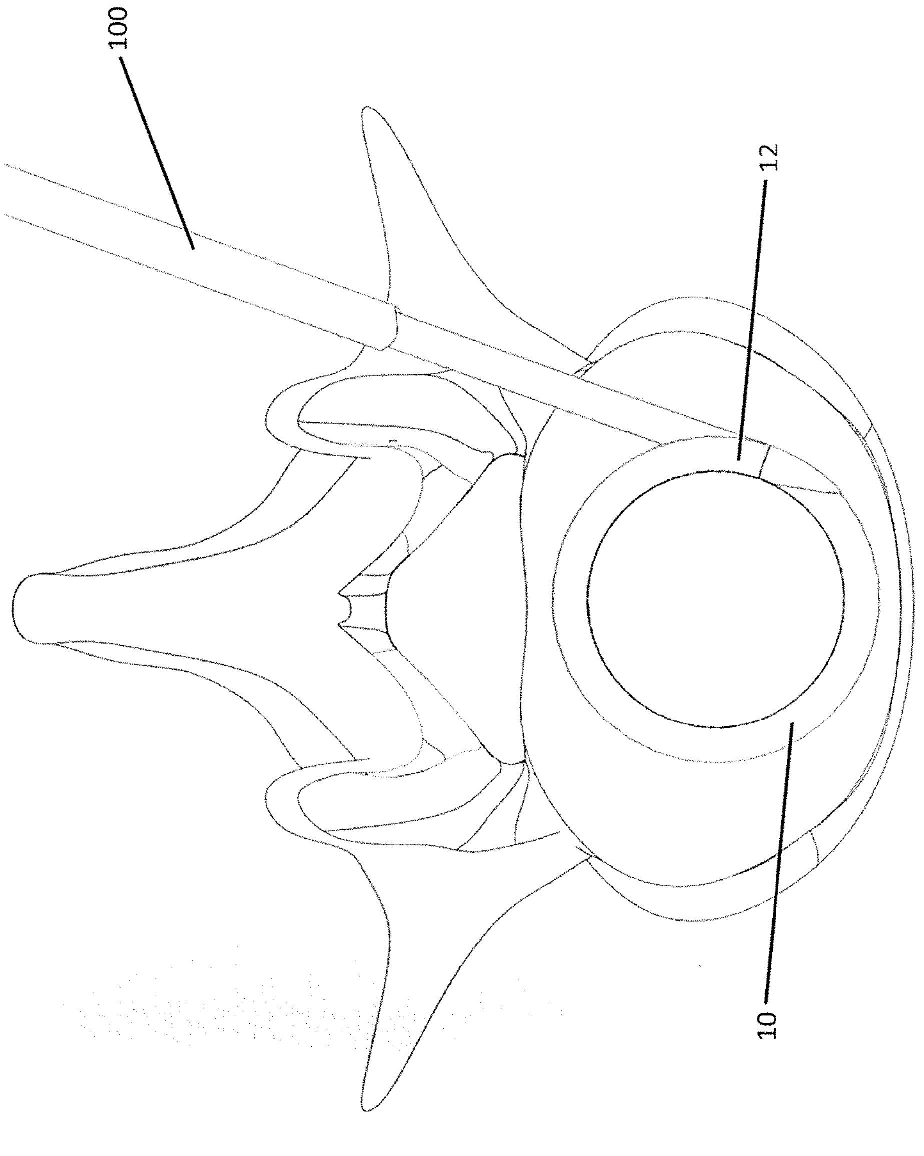
FIG. 3A shows a vertebrae with a coiled implant positioned on central area of the vertebral endplate.
Figure 3B:
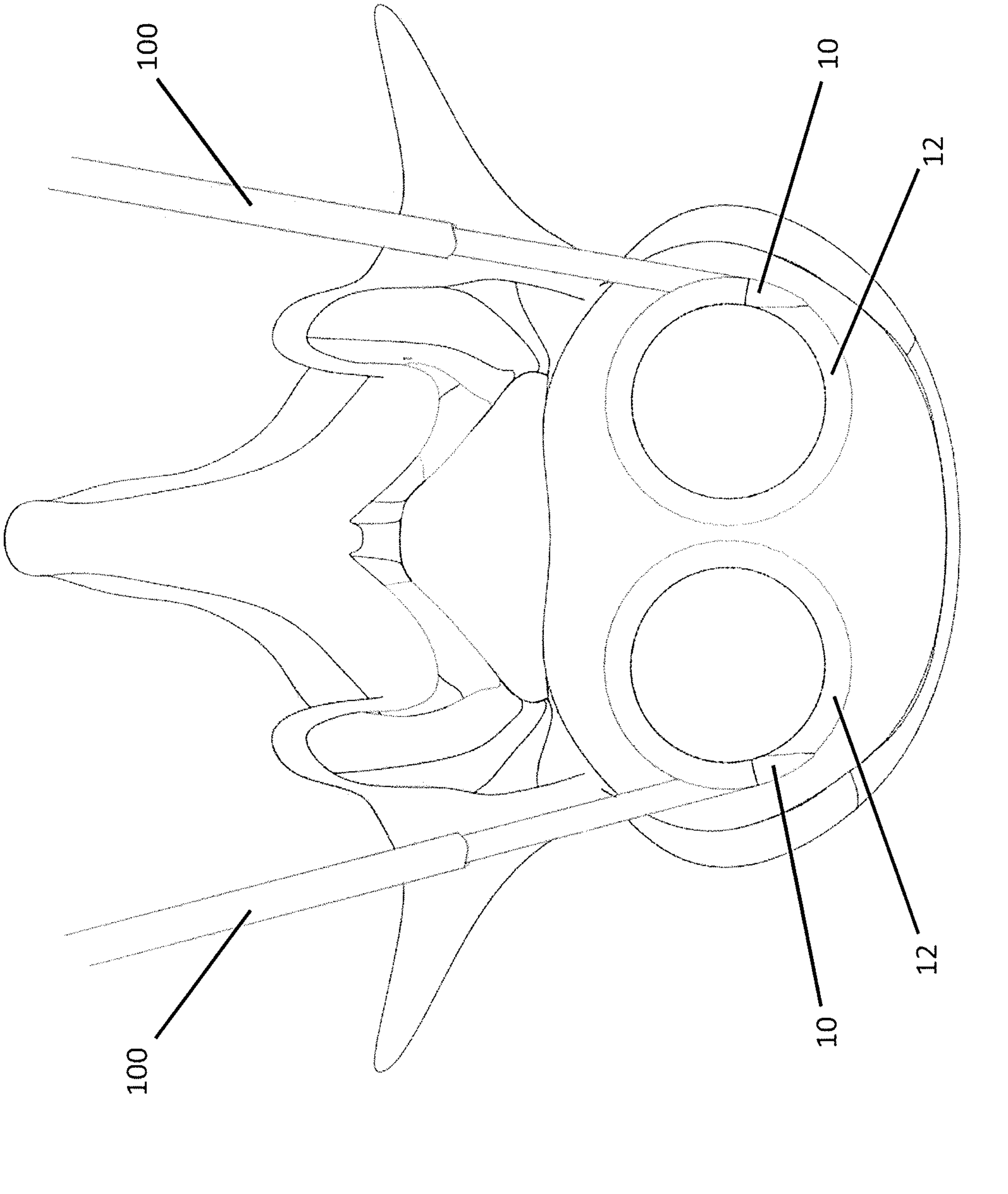
FIG. 3B shows a vertebrae with two coiled implants, each positioned at a lateral area of the vertebral endplate.
Figure 4:
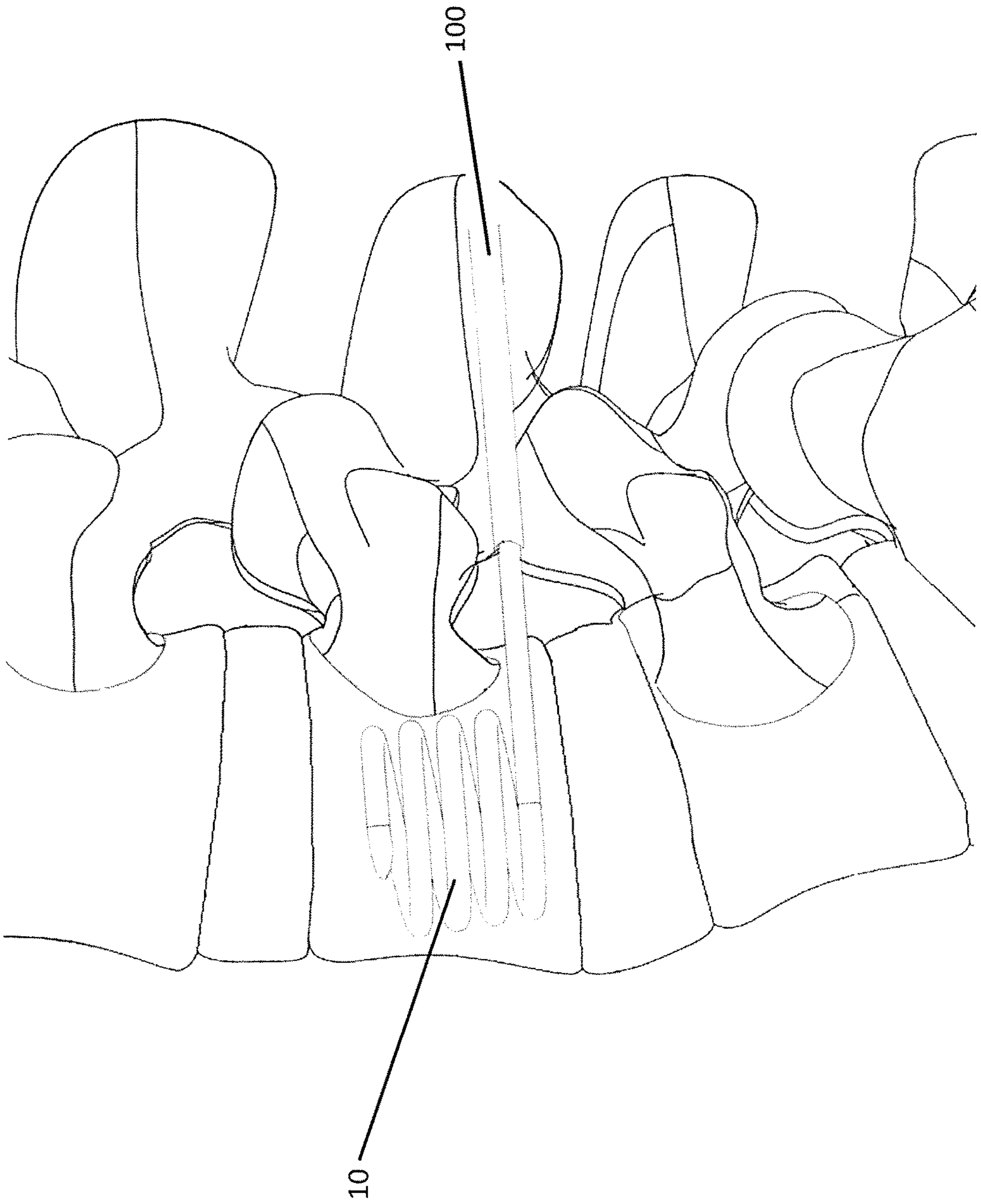
FIG. 4 shows a coiled implant in the place of a vertebral body removed from a copectomy procedure.

More than one coiled implant 10 may be implanted into the intervertebral space or into the vertebral body. Although one coiled implant 10 may be used in some aspects, two, or even three implants 10 may be implanted in some aspects. The coiled implant 10 may be placed at the anterior area, posterior area, or lateral area of the vertebral endplate, including in the anterior-lateral or posterior-lateral areas of the vertebral endplate, see, e.g., FIG. 3A. Where more than one implant 10 is used, one implant 10 may be placed in the anterior area, and a second implant 10 may be placed in the posterior area (see, e.g., FIG. 3B), or one implant 10 may be placed on one lateral area and the second implant 10 may be placed in the opposing lateral area.

Once the implant 10 is in place, the balloon 30 or membrane 30 may be filled to a desired level with air or a fluid, thereby expanding the height H of the coil by forcing the loops 16 that the balloon 30 or membrane 30 touches to move upward and downward about the axis X of the implant 10. The axis X preferably approximates the vertical orientation of the spine of the subject, for example, the vertical spine of a human being that walks upright. In some aspects, for example, where the subject is an animal that walks on four legs, the axis X may approximate the horizontal orientation of the spine of the subject. The air or fluid may be supplied by the second tool 200.

In some aspects, once the implant 10 is in place, but before the balloon 30 or membrane 30 is filled with air or fluid, the balloon 30 or membrane 30 may be filled with a contrast solution such as a radiocontrast solution, such that the coiling (if inserted uncoiled with coiling in situ) and/or placement of the implant 10 may be visualized and confirmed before permanence is established, for example, by filling the balloon with a permanent air or fluid and/or by deploying a bone graft material or bone cement. Filling the balloon 30 or membrane 30 with a contrast solution may also be used to visualize and confirm that the balloon 30 or membrane will properly deploy out of the gap 26 and/or into spaces 18. The contrast solution is preferably removed from the balloon 30 or membrane 30 before the balloon 30 or membrane 30 is filled with air or fluid.

The level of air or fluid may vary according to the needs of the subject, including the proper restored height of the intervertebral space, or the proper reconstructed height of the vertebral body. In some aspects, more than one balloon 30 or membrane 30 is present in the coiled implant 10, or a single balloon 30 or membrane 30 with more than one chamber is present in the coiled implant. In such aspects, a first balloon 30 or membrane 30, or a first chamber of the balloon 30 or membrane 30, may be filled to one level and at least a second balloon 30 or membrane 30, or second chamber of the balloon 30 or membrane, may be filled to another level that is greater or less than the level of the first balloon 30 or membrane or first chamber, so as to establish a lordotic angle in the intervertebral space. In other words, with one balloon 30 or membrane 30, or with one chamber of a single balloon 30 or membrane 30, filled to one level, and the other balloon 30 or membrane, or other chamber of a single balloon 30 or membrane 30, filled to another level, the expanded height H of the coiled implant 10 differs on at least to sides and this difference in height H among these sides establishes a desired angle of lordosis.

Before, after, or concomitant with the filling of the balloon(s) 30 or membrane(s) 30, a bone graft material may be deployed from the implant 10. For example, a bone graft material may be inserted into an opening 15 or 17, for example, by way of the first tool 100, into the lumen 22, out from the plurality of apertures 24 and, optionally also from the other opening 15 or 17, and into the intervertebral space. Upon deployment, the bone graft material may be present on and about the exterior of the coil, and/or may be present on and about the interior or the coil, including the central void 19 established by the loops 16 and balloon 30 or membrane 30. In some aspects, the bone graft material is pre-loaded into the lumen 22, and air, water, or saline is forced into the opening 15 or 17, thereby forcing the bone graft material out of the apertures 24. The bone graft material remains in place and facilitates osseointegration of the implant, and in some aspects, may facilitate fusion of the adjacent vertebrae as bone begins to form off of the bone graft material.

In some optional embodiments, the coiled implant 10 is removed from the subject after the balloon 30 or membrane 30 is filled. In which case, the balloon 30 or membrane 30 is retained and supports disc replacement or vertebral body reconstruction. If the coiled implant 10 remains, the implant 10 and balloon 30 or membrane 30 supports disc replacement or vertebral body reconstruction. The implant 10 and/or balloon 30 or membrane 30 serve as the missing disc or missing vertebral bone until osseointegration and fusion, mediated by bone graft material, proceeds sufficiently.

The disclosure is not limited to the embodiments described and exemplified above, but is capable of variation and modification within the scope of the appended claims.

What is claimed:

1. A surgical method, comprising:

inserting an implant into a patient, the implant comprising an expandable hollow coil having a first end, a second end, and sidewalls defining a lumen passing therethrough, the lumen having at least one coiled balloon disposed therein;

deploying the balloon from the lumen of the coil into at least some of the spaces between adjacent loops of the coil to increase a height of the coil; and inserting a guidewire into the patient, wherein the implant is inserted over the guidewire and re-coiled as the guidewire is removed therefrom.

2. The method of claim 1, wherein inserting the implant comprises delivering the coil through a cannula while the coil is in an uncoiled state.

3. The method of claim 1, wherein inserting the implant comprises inserting the implant into a vertebral body.

4. The method of claim 1, wherein inserting the implant comprises inserting the implant into an intervertebral disc space.

5. The method of claim 1, wherein deploying the balloon comprises inflating the balloon with a fluid.

6. The method of claim 1, wherein the sidewall is C-shaped such that a gap is formed in the sidewall and wherein deploying the balloon comprises deploying the balloon through the gap formed in the sidewall.

7. The method of claim 1, further comprising delivering a bone graft material or bone cement through the implant.

8. The method of claim 7, wherein the bone graft material or bone cement is delivered to a central void defined by the coil.

9. The method of claim 7, further comprising removing the coil from the patient after delivering the bone graft material or bone cement.

10. The method of claim 9, wherein the balloon is left in the patient after the coil is removed.

11. A surgical method, comprising:

inserting a guidewire into a patient;

inserting an expandable coil into the patient over the guidewire, the expandable coil comprising a hollow tube having a first end, a second end, and sidewalls that define a lumen, the hollow tube being formed into a plurality of loops stacked in a height dimension as the guidewire is removed therefrom, the plurality of loops having a space between lower and upper sidewalls of vertically adjacent loops such that the lumen has a coiled shape;

deploying a balloon into at least some of the spaces between vertically adjacent loops; and filling the balloon to expand the coil in the height dimension.

12. The method of claim 11, wherein the coil, when expanded, has a height that approximates the height of an intervertebral disc, the height of a vertebral body, or the height of a spinal motion segment.

13. The method of claim 11, wherein the coil includes a plurality of apertures that pass through the sidewalls and into the lumen.

14. The method of claim 11, wherein the sidewalls comprise a gap though the sidewalls and into the lumen.

15. The method of claim 14, wherein the gap runs substantially the entire length of the coil.

16. The method of claim 11, wherein the coil is inserted into the patient in an uncoiled orientation.

17. The method of claim 11, further comprising delivering bone graft material or bone cement through the lumen.

* * * * *